(12) United States Patent
Matsuno

(10) Patent No.: US 7,606,406 B2
(45) Date of Patent: Oct. 20, 2009

(54) IMAGING METHOD AND APPARATUS

(75) Inventor: Hiroyuki Matsuno, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 770 days.

(21) Appl. No.: 10/869,531

(22) Filed: Jun. 16, 2004

(65) Prior Publication Data

US 2004/0258292 A1    Dec. 23, 2004

(30) Foreign Application Priority Data

Jun. 19, 2003    (JP)    ............................. 2003-175238

(51) Int. Cl.
*G06K 9/00*    (2006.01)
(52) U.S. Cl. ..................................... 382/132
(58) Field of Classification Search ................ 382/271, 382/128, 132; 348/231.1
See application file for complete search history.

(56) References Cited

U.S. PATENT DOCUMENTS

| | | | | |
|---|---|---|---|---|
| 5,301,220 A * | 4/1994 | Wong | .......................... | 348/162 |
| 6,021,393 A * | 2/2000 | Honda et al. | .................... | 705/3 |
| 6,445,409 B1 * | 9/2002 | Ito et al. | ...................... | 348/155 |
| 6,643,416 B1 * | 11/2003 | Daniels et al. | ............... | 382/299 |
| 6,765,204 B2 * | 7/2004 | Sasajima et al. | ............. | 250/310 |
| 6,810,108 B2 * | 10/2004 | Clark et al. | .................... | 378/65 |
| 6,819,786 B2 * | 11/2004 | Hirai | ........................... | 382/132 |
| 7,003,145 B2 * | 2/2006 | Polkus et al. | ................ | 382/132 |
| 7,046,232 B2 * | 5/2006 | Inagaki et al. | ................ | 345/158 |

FOREIGN PATENT DOCUMENTS

| | | |
|---|---|---|
| JP | 06-078910 | 3/1994 |
| JP | 06-325143 | 11/1994 |
| JP | 07-052284 | 2/1995 |
| JP | 07-141529 | 6/1995 |
| JP | 10-243456 | 9/1998 |
| JP | 2000-033082 | 2/2000 |
| JP | 2003-116845 A | 4/2003 |

OTHER PUBLICATIONS

Communication from Japanese Patent Office (JPO) issued Dec. 5, 2008 in reference to Japanese Patent Application No. 2003-175238, which is a foreign counterpart to the present application. (2 pages in Japanese language are provided herewith).

(Continued)

*Primary Examiner*—Matthew C Bella
*Assistant Examiner*—Dennis Rosario
(74) *Attorney, Agent, or Firm*—Cowan, Liebowitz & Latman, P.C.

(57) ABSTRACT

When an operator presses an exposure switch in step S104, X-ray imaging is executed. Radiation field recognition is performed in step S105. In step S106, density adjustment is performed by obtaining characteristic features of an image in the radiation field. The density-adjusted image is displayed on a display unit in step S107. If the operator gives a crop instruction in step S108, the flow advances to step S109 to check the image size of the designated and extracted region. At the same time, characteristic features are extracted from the image. That is, in the embodiments, it is checked whether an image in an extracted region has characteristic features attached an imaging method button for "finger". If it is determined in step S110 that the extracted region is valid, the flow advances to step S115. If it is determined that the region is invalid, the flow advances to step S111 to execute notification processing.

10 Claims, 7 Drawing Sheets

OTHER PUBLICATIONS

Japanese Office Action dated Apr. 18, 2008 for Japanese Patent Application No. 2003-175238, which is the foreign counterpart of the present application. (Japanese Language provided).

Japanese Office Action dated Aug. 22, 2008 for Japanese Patent Application No. 2003-175238, which is the foreign counterpart of the present application. (Japanese Language provided).

* cited by examiner

FIG. 2

| SELECT PATIENT | | |
|---|---|---|
| PATIENT ID | PATIENT NAME | IMAGING PORTION |
| 0001 | TARO YAMADA | CHEST IN PA AND LATERAL POSITION |
| 0002 | HANAKO KAWADA | FINGER |
| ... | ... | .... |

30

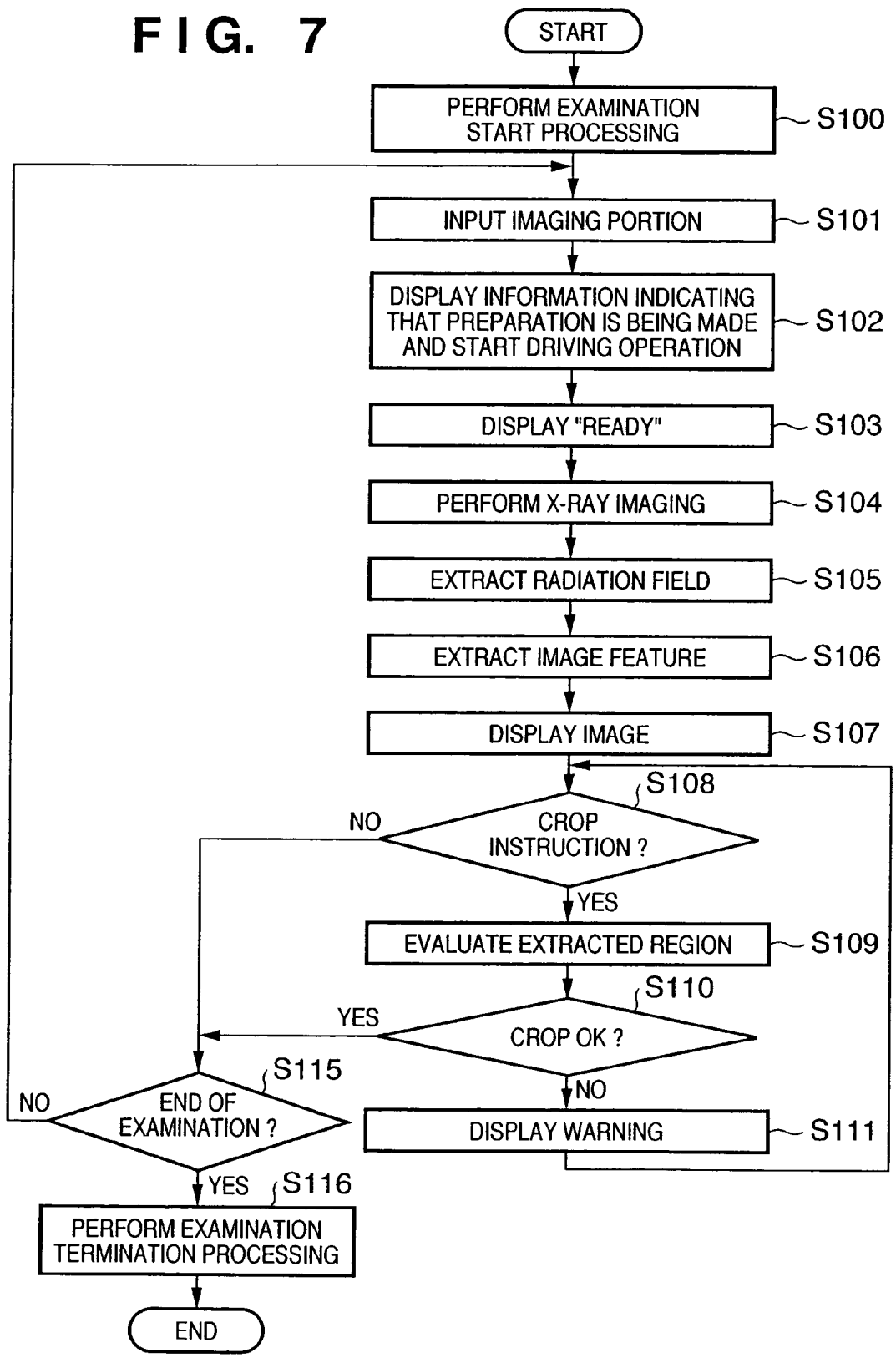

IMAGING METHOD AND APPARATUS

FIELD OF THE INVENTION

The present invention relates to an X-ray digital imaging method and apparatus.

BACKGROUND OF THE INVENTION

Conventionally, a film screen system formed by combining an intensifying screen with a radiographic film has been widely used for X-ray imaging aimed at medical diagnosis. A film is designed to enhance the contrast in a density range in which a portion to be diagnosed can be easily observed when a film image obtained by X-ray imaging is observed on a film viewer. However, deviations from the designed imaging conditions tend to cause overexposure or underexposure, resulting in affecting diagnosis.

Recently, an X-ray digital imaging apparatus has begun to be used, which employs a flat panel detector (to be referred to as an FPD hereinafter) which converts X-rays into electrical signals proportional to the intensities of the X-rays. According to this imaging apparatus, an image of a subject to be examined is obtained by imaging by an X-ray detector having a large area. A region irradiated with X-rays is then detected from the entire image region by an image processing technique, and a characteristic feature of the image is extracted, thereby performing density adjustment. This can therefore solve the conventional problem concerning exposure adjustment (see, for example, Japanese Patent Publication No. 7-52284). In addition, since a designated region is extracted from the entire image region, invalid digital information can be deleted, and the amount of information stored can be reduced. This apparatus also has a function for improving diagnostic performance by image processing such as image enhancement.

The above radiation field recognition is, however, implemented by a program, and 100% success for radiation field recognition cannot be expected unless an imaging method based on the X-ray dose, the position of a subject to be imaged, and the like intended by the program is executed. That is, when imaging is performed under exceptional conditions, a crop region must be manually corrected.

When a crop region is to be designated in accordance with an instruction from an operator as described above, an excessively small crop region may be designated due to human errors in operating a mouse and touch panel. The operator often gives his/her attention to the density of an image. If, therefore, the density is stable by chance, and the operator terminates the imaging operation without any concern for the validity of the crop region, an invalid image may be transmitted to an external printer or image storage device, or an image display device.

SUMMARY OF THE INVENTION

The present invention has been made in consideration of the above problem, and has as its object to provide a technique of preventing an image region extracted by an operator from an image obtained by imaging from being processed as an invalid region, and notifying the operator that the designated image region is not valid.

In order to solve the above problem and achieve the above object, according to the present invention, there is provided an imaging apparatus comprising designation means for designating a predetermined image region from an image obtained by imaging, determination means for determining whether or not a region designated by the designation means is a valid region, and notification means for notifying a determination result obtained by the determination means.

In addition, according to the present invention, there is provided an imaging method comprising a designation step of designating a predetermined image region from an image obtained by imaging, a determination step of determining whether or not the region designated in the designation step is a valid region, and a notification step of notifying a determination result obtained in the determination step.

Preferably, in the above apparatus or method, the determination means (step) determines whether the number of pixels in the image region designated by the designation means (step) in a vertical direction or a horizontal direction is smaller than a threshold set in advance for each portion to be imaged, and if the number of pixels is smaller than the preset threshold, the notification means (step) performs notification.

Preferably, in the above apparatus or method, the determination means (step) determines whether an area of the image region designated by the designation means (step) is smaller than a preset threshold, and if the area is smaller than the preset threshold, the notification means (step) performs notification.

Preferably, the determination means (step) determines whether the image region designated by the designation means (step) has a parameter feature attached to a pre-designated image, and if the image region does not have the feature, the notification means (step) performs notification.

Preferably, the notification means (step) changes a color of the image region designated by the designation means (step) to notify that the region is not a valid region.

Furthermore, according to the present invention, there is provided an imaging apparatus comprising designation means (step) for designating a predetermined image region from an image obtained by imaging, evaluation means for evaluating whether or not the region designated by the designation means is a valid region, and setting means for re-setting the designated region to a preset region size on the basis of an evaluation result obtained by the evaluation means.

Moreover, according to the present invention, there is provided an imaging method comprising a designation step of designating a predetermined image region from an image obtained by imaging, an evaluation step of evaluating whether or not the region designated in the designation step is a valid region, and a setting step of re-setting the designated region to a preset region size on the basis of an evaluation result obtained in the evaluation step.

Preferably, in the above apparatus or method, the setting means (step) obtains a center of gravity of the image region designated by the designation means (step) and re-sets the designated region to a preset region size, centered on the center of gravity.

Note that the present invention can be realized as a program for executing a computer to execute the above imaging method or a computer-readable storage medium storing a program for causing a computer to execute the above imaging method.

As described above, the present invention can prevent an image region extracted by an operator from an image obtained by imaging from being processed as an invalid region, and notify the operator that the designated image region is not valid.

Other objects and advantages besides those discussed above shall be apparent to those skilled in the art from the description of a preferred embodiment of the invention which follows. In the description, reference is made to accompanying drawings, which form a part thereof, and which illustrate an example of the invention. Such example, however, is not exhaustive of the various embodiments of the invention, and therefore reference is made to the claims which follow the description for determining the scope of the invention.

BRIEF DESCRIPTION OF THE DRAWINGS

FIG. 2 is a view showing a display example of an imaging order list on a display unit;

FIG. 7 is a flowchart showing a crop region control method.

DETAILED DESCRIPTION OF THE PREFERRED EMBODIMENTS

The embodiments of the present invention will be described in detail below with reference to the accompanying drawings.

First Embodiment

Figure 1:
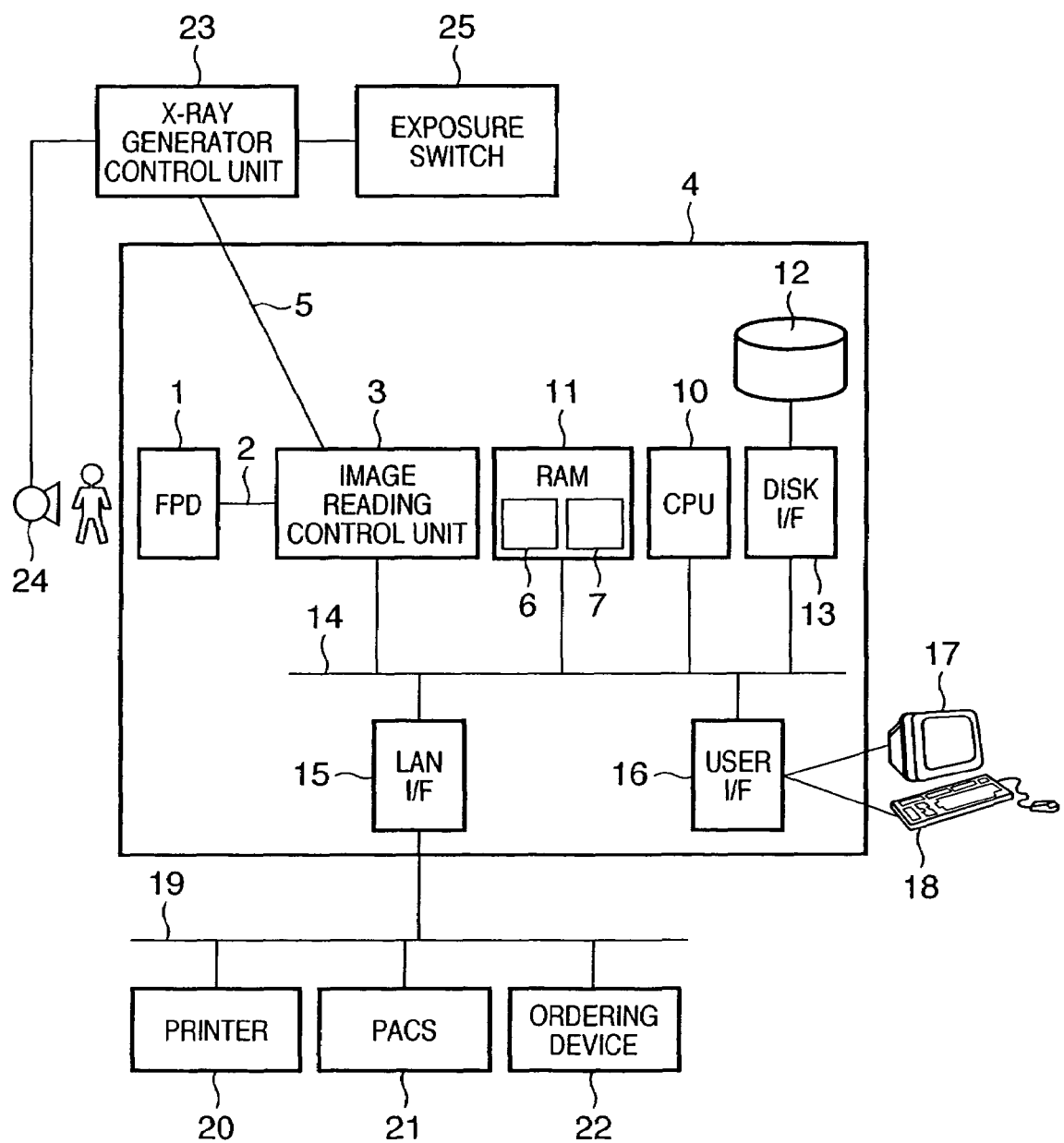
FIG. 1 is a block diagram showing the system configuration of an imaging apparatus according to an embodiment of the present invention.

FIG. 1 is a block diagram showing the system configuration of an imaging apparatus according to an embodiment of the present invention.

As shown in FIG. 1, the imaging apparatus according to this embodiment is an example of applying the present invention to a medical X-ray digital imaging apparatus which performs imaging by using radiation such as X-rays. This apparatus includes an FPD 1 having a phosphor and large-screen photoelectric conversion device, an image reading control unit 3 which stores image data upon establishing synchronism with exposure controlled by an X-ray generator control unit 23, a CPU 10, a RAM 11 which stores a control program, a hard disk 12 which stores images obtained by imaging, a disk interface (I/F) 13, a user I/F 16 with an operator, and a communication LAN I/F 15 with an external apparatus. Note that the present invention can be applied to imaging apparatuses other than X-ray imaging apparatuses.

In an X-ray imaging apparatus 4, the host CPU 10 executes the control program according to this embodiment. The RAM 11 stores the control program according to the embodiment. A control program 6 is loaded from the hard disk 12 and operated on the RAM 11 serving as a work area by the CPU 10. Reference numeral 7 denotes a RAM for temporarily storing an image obtained by imaging and ensured on the RAM 11.

The FPD 1 is connected to the image reading control unit 3 through a data line 2 for power, image transfer and control signals. The hard disk 12 stores the control program according to this embodiment which is operated by the host CPU 10. The hard disk 12 also serves to temporarily store correction information necessary for imaging and an image obtained by imaging. Reference numeral 14 denotes an internal bus of the X-ray imaging apparatus 4. The LAN I/F 15 is used to receive an imaging order from an external ordering device 22 or transmit an image obtained by imaging to a printer 20 or PACS 21 as an external device so as to allow the use of the image for diagnosis.

The user I/F 16 includes a display device 17 and an input device 18 including a keyboard, mouse, and the like, and interfaces with the operator of the X-ray imaging apparatus. Obviously, the display and input devices 17 and 18 may be replaced with a touch panel device.

First of all, the CPU 10 of the X-ray imaging apparatus 4 receives ordering information from a radiology information system (RIS) through the ordering device 22 on a LAN 19. In this embodiment, a list of received ordering information is displayed on the display device 17 through the user I/F, as shown in FIG. 2. When the radiographer, who is the operator of the X-ray imaging apparatus, selects the examination indicated by reference numeral 30 with the input device 18, the control program 6 executed by the CPU 10 changes the window displayed on the display device 17 such as a CRT or liquid crystal display, and displays imaging order information in detail.

Figure 3:
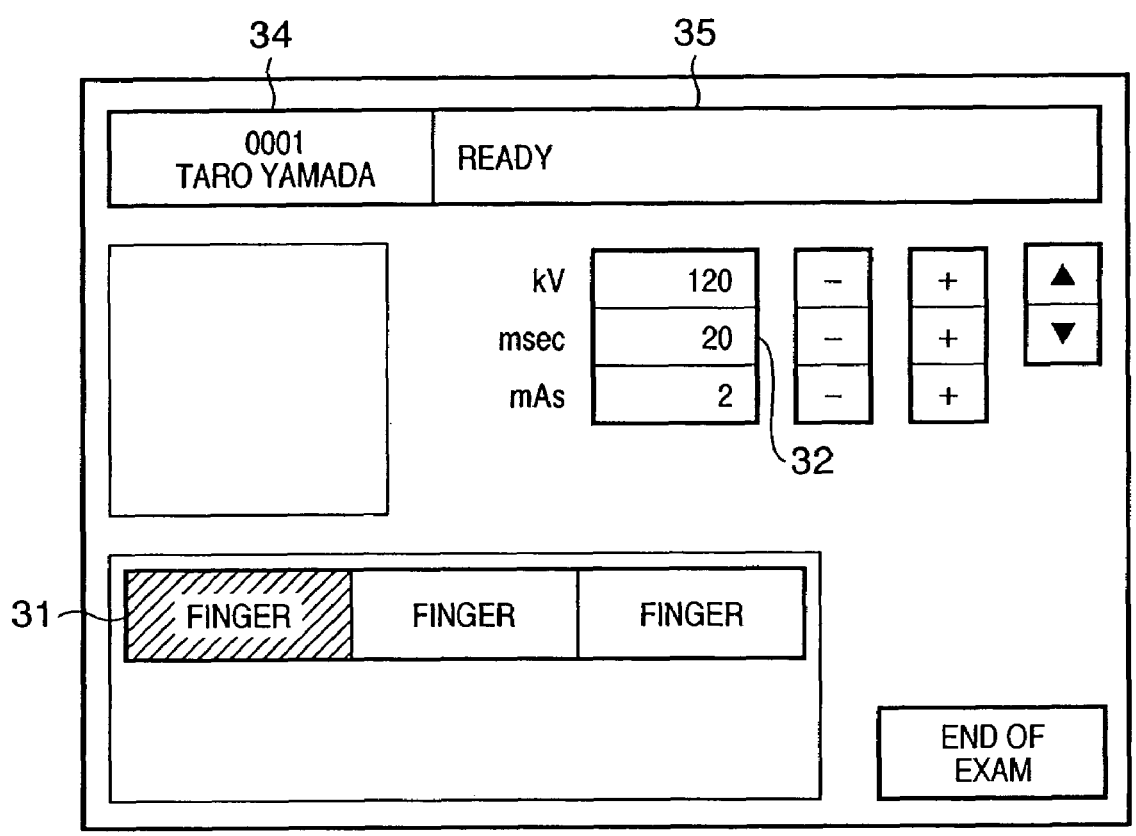
FIG. 3 is a view showing an example of an imaging window on the display unit.

FIG. 3 is a view showing a display example on the display device 17 according to an embodiment of the present invention.

The CPU 10 displays patient information, for example, a patient ID, name, date of birth, and the like in a region 34 to present the operator the selected examination 30. The CPU 10 also displays an imaging order constituted by imaging portions received from the ordering device 22 in an imaging reservation tray 31. In this embodiment, for example, three images of "finger" are to be taken by imaging. Reference numeral 32 denotes an imaging condition corresponding to a button representing the imaging order described above; and 35, a region which is used to display the state of the X-ray imaging apparatus.

The above imaging order button corresponds to image processing parameters and imaging conditions suitable for an individual imaging method. These parameter and conditions are stored in a database (DB) in the hard disk 12 serving as a storage device. When the operator presses an imaging method button, the control program according to this embodiment reads out imaging conditions and image processing parameters from the DB, and determines them as imaging conditions to be used. The control program 6 then stores the imaging conditions in the RAM and uses them for imaging control.

The CPU 10 starts imaging operation and sets the first imaging portion of the ordering information denoted by reference numeral 31, i.e., the "finger" button, in a selectable state. The operator places a patient to be imaged between the FPD 1 and an X-ray tube 24 and adjusts his/her position to an imaging position. In the meantime, the CPU 10 applies a voltage to the FPD 1 and issues an imaging preparation command to perform X-ray imaging by the FPD 1 in accordance with the system control program 6. The control program for the FPD 1 receives the command and shifts the state of the FPD to a ready state for X-ray imaging. After a wait of several seconds until noise due to a dark current decreases, the control program 6 detects that the FPD 1 is set in a ready state for X-ray imaging, and displays "READY" in the region 35.

Upon confirming on the window that the FPD 1 is in the ready state for imaging, the operator presses an exposure switch 25 to input a trigger for generating X-rays to the system. An exposure signal generated by the exposure switch 25 is input to the image reading control unit 3 through a sync signal line 5. The image reading control unit 3 starts storing operation in accordance with the drive timing of the FPD 1 in the state of a control signal 2. At the same time, the image reading control unit 3 generates an exposure permission signal 5. The exposure permission signal 5 is returned to the X-ray generator control unit 23. The X-ray generator control unit 23 then causes the X-ray tube 24 to generate X-rays.

Figure 4:
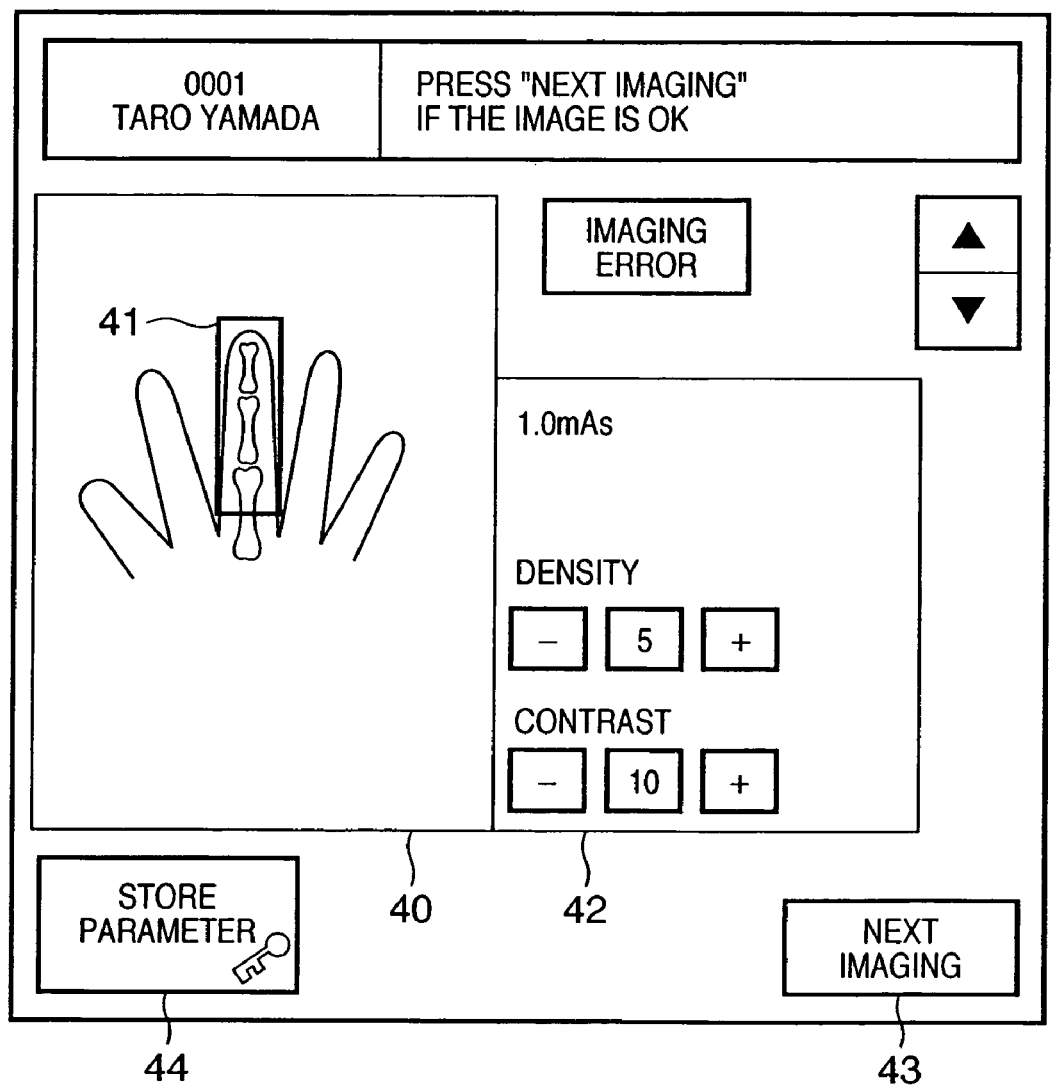
FIG. 4 is a view showing the state of the display unit after imaging.

This system acquires an X-ray image as digital data which has been transmitted through the patient upon exposure of X-rays, and transfers the image to the image reading control unit 3. The CPU 10 then executes the control program 6 to change the window of the user I/F unit as shown in FIG. 4. At this time, radiation field recognition is performed for the image obtained by X-ray imaging and acquired from the FPD 1 by using image processing parameters determined before imaging. Thereafter, automatic portion analysis processing is performed to search the image for a characteristic feature of "finger", thereby performing automatic density adjustment. When the analysis is successfully done, the determined radiation field is displayed as indicated by reference numeral 41 in FIG. 4, and density and contrast parameters in the region are presented to the operator. The operator confirms that the density and contrast in the selected region are stable, and presses a parameter storage button 44 to input information indicating an imaging success to the system.

The CPU 10 displays the image data acquired from the image reading control unit 3 in a region 40, and displays X-ray generating conditions as imaging execution information in a region 41 on the user I/F. The CPU 10 also stores the conditions in the hard disk 12.

Reference numeral 42 denotes parameter buttons for adjusting the density and contrast of an image obtained by imaging. The X-ray imaging apparatus 4 performs image analysis in accordance with the control program executed by the CPU 10, and automatically analyze the density of the image. If there is a problem in automatic density adjustment for the image displayed in the region 40, the operator can change the contrast and density of the image obtained by imaging by adjusting the parameter buttons 42.

Upon confirming the image obtained by imaging on the window shown in FIG. 4, the operator presses a "next imaging" button 43 on the window to perform next imaging operation. The window shown in FIG. 3 is then restored. The user I/F 16 is used to select the next ordered imaging portion.

The CPU 10 makes the operator repeatedly execute the same flow of imaging as that described above until the entire imaging order is complete. When the imaging order is complete, since there is no next imaging operation, the CPU 10 changes the button indicated by reference numeral 43 into "end of examination". The operator can terminate the examination on the patient by pressing the button 43.

When the examination is terminated, the control program 6 transmits the imaging conditions and imaging execution information stored in the hard disk 12 to the ordering device 22. The control program 6 notifies the ordering device 22 of the end of imaging for the examination in accordance with a predetermined communication protocol.

The control program 6 outputs the image obtained by imaging as image data having the above imaging conditions and imaging execution information as additional information to a DICOM (Digital Imaging & Communications in Medicine) in accordance with a standard medical communication protocol. In order to check the image obtained by imaging, the radiographer checks a diagnosis image on an image display device spaced apart from the X-ray imaging apparatus, and also check the quality of the output film. The resultant image is then used by a doctor for diagnosis.

Figure 5:
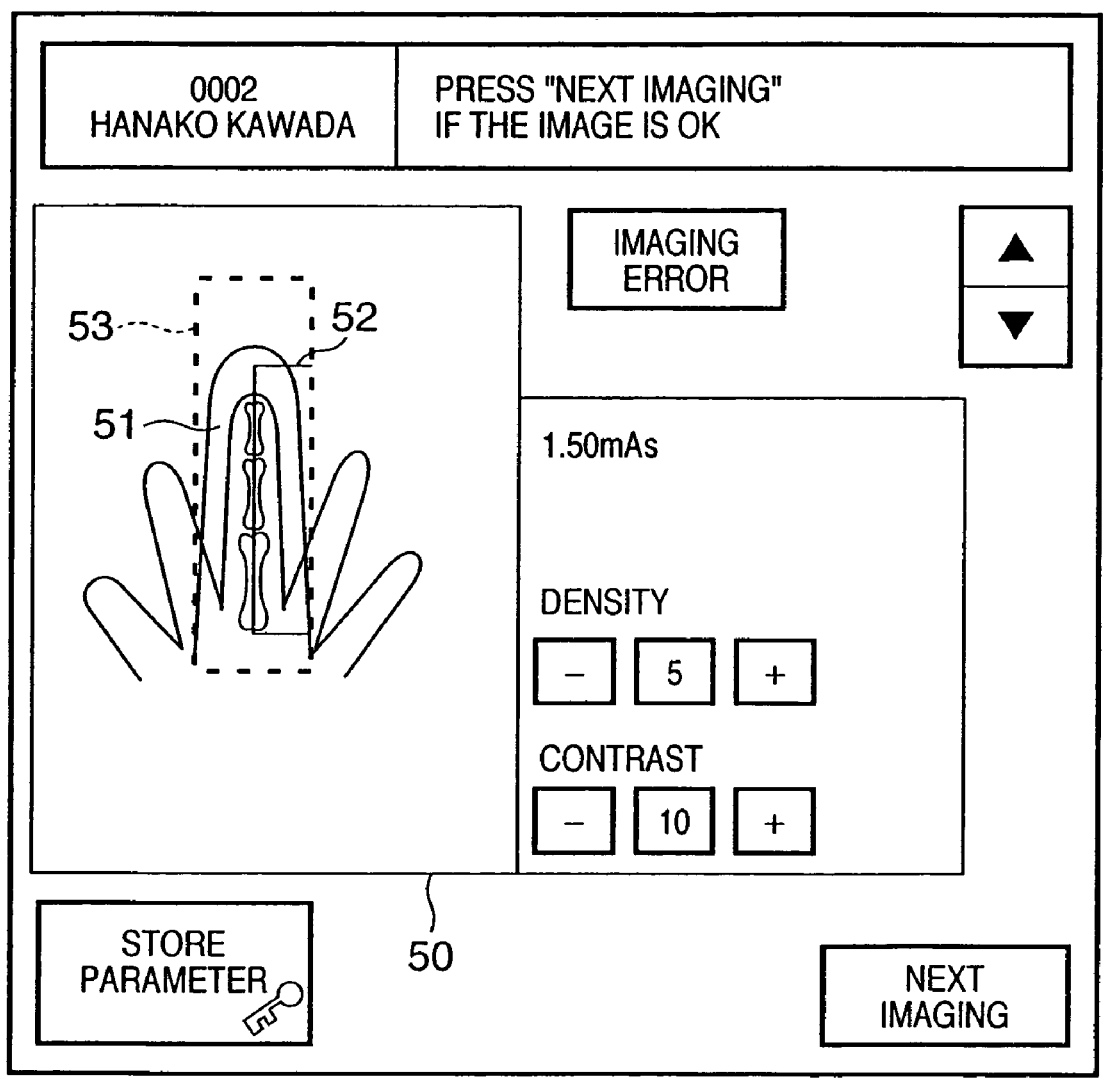
FIG. 5 is a view showing a display example at the occurrence of a radiation field recognition error.

If, however, a subject to be examined has a plaster cast 51 or a metal embedded in the body, as shown in FIG. 5, a histogram in a radiation field may greatly vary from a normal image, and density instability may occur. In addition, embedding a metal piece may cause a failure in radiation field recognition due to the influences of scattered X-rays. For such a case, there has been proposed a method of performing radiation field recognition again by removing the pixel value of a portion regarded as a metal portion which transmits no X-rays from a histogram. This method, however, is not an infallible measure. For this reason, in an exceptional image obtained by imaging, the operator inevitably repeats designating a valid image region from the image manually displayed on a window. Such a situation occurs several times a day. If a portion 52 is recognized as a radiation field instead of a real radiation field 53, and displayed as shown in FIG. 5, the operator needs to perform correcting operation. Assume that the operator sends information indicating the completion of imaging to the subsequent step in spite of a failure in extracting a valid region without noticing the failure, because of accidental density stability. In this case, an image that cannot be used for diagnosis is sent out to an external apparatus, resulting in recorrection and retransmission. This increases the wait times for the patient and doctor, and hence leads to time loss.

The processing of determining whether an image region which is designated by an operator and extracted is a valid region and notifying the determination result will be described with reference to the flowchart of FIG. 7.

When the operator presses a button indicating an imaging portion on the window, imaging conditions and image processing parameters are acquired from the DB which stores imaging parameters and are stored in the program RAM by the program according to this embodiment which is executed by the CPU.

When the operator gives an examination start instruction, patient data and an imaging order are acquired from the ordering device 22 and displayed on the window in step S100. The flow then advances to step S101, in which the operator presses the imaging method button on the window to acquire image processing parameters for the imaging method from the DB. In order to set the sensor in a "READY" state, the flow advances to step S102, in which information indicating that preparation is being made is displayed on the window, and imaging preparation driving is started. When the dark current in the FPD sufficiently decreases, the flow advances to step S103 to display, on the window, information indicating that imaging can be performed. In step S104, when the operator presses the exposure switch, X-ray imaging is executed.

After an original image is acquired from the FPD, radiation field extraction is performed in step S105. As a radiation field extraction method in this embodiment, for example, a method like that disclosed in Japanese Patent Laid-Open No. 10-243456 is used. In this method, profiles of a target image are taken at predetermined intervals, and the most frequently occurred point sequence is extracted as a radiation field boundary from the radiation field boundaries predicted from the respective profiles.

A direct exposed region extracting unit (not shown), which detects the portion of direct irradiation that has no subject, executes part of the processing in step S105. If a target image has a radiation field stop, a radiation field image is extracted from a reduced image of 168×168 pixels generated from an original image from the FPD and supplied as an image with a smaller size to the direct exposed region extracting unit. If a target image has no radiation field stop, an entire reduced image of 168×168 pixels is supplied as a radiation field image to the direct exposed region extracting unit.

The direct exposed region extracting unit specifies a region, of the radiation field image extracted by a radiation field extraction unit in step S105, in which the X-ray dose is high from the histogram, and recognizes a concatenated state from the periphery of the region, thereby determining a direct exposed region of the radiation field image (a region directly irradiated with X-rays). The information indicating the direct exposed region obtained by the direct exposed region extracting unit is supplied, together with the radiation field image as the target image, to the feature amount extraction processing in step S106.

Subsequently, in step S106, density adjustment is performed by obtaining a characteristic feature of the image in the radiation field. The feature amount extracting unit extracts the shape of the reduced image and a plurality of feature amounts thereof on the basis of the radiation field image and its direct exposed region from the radiation field extraction processing in step S105, and displays the original image whose density is adjusted on the basis of the feature amounts on the display unit in step S107.

When the operator gives a crop instruction in step S108, the flow advances to step S109 to check the image size in the designated cropped region. At the same time, characteristic features are extracted from the image. That is, in this embodiment, the image in the cropped region has characteristic features attached to the imaging method button for "finger".

Figure 6:
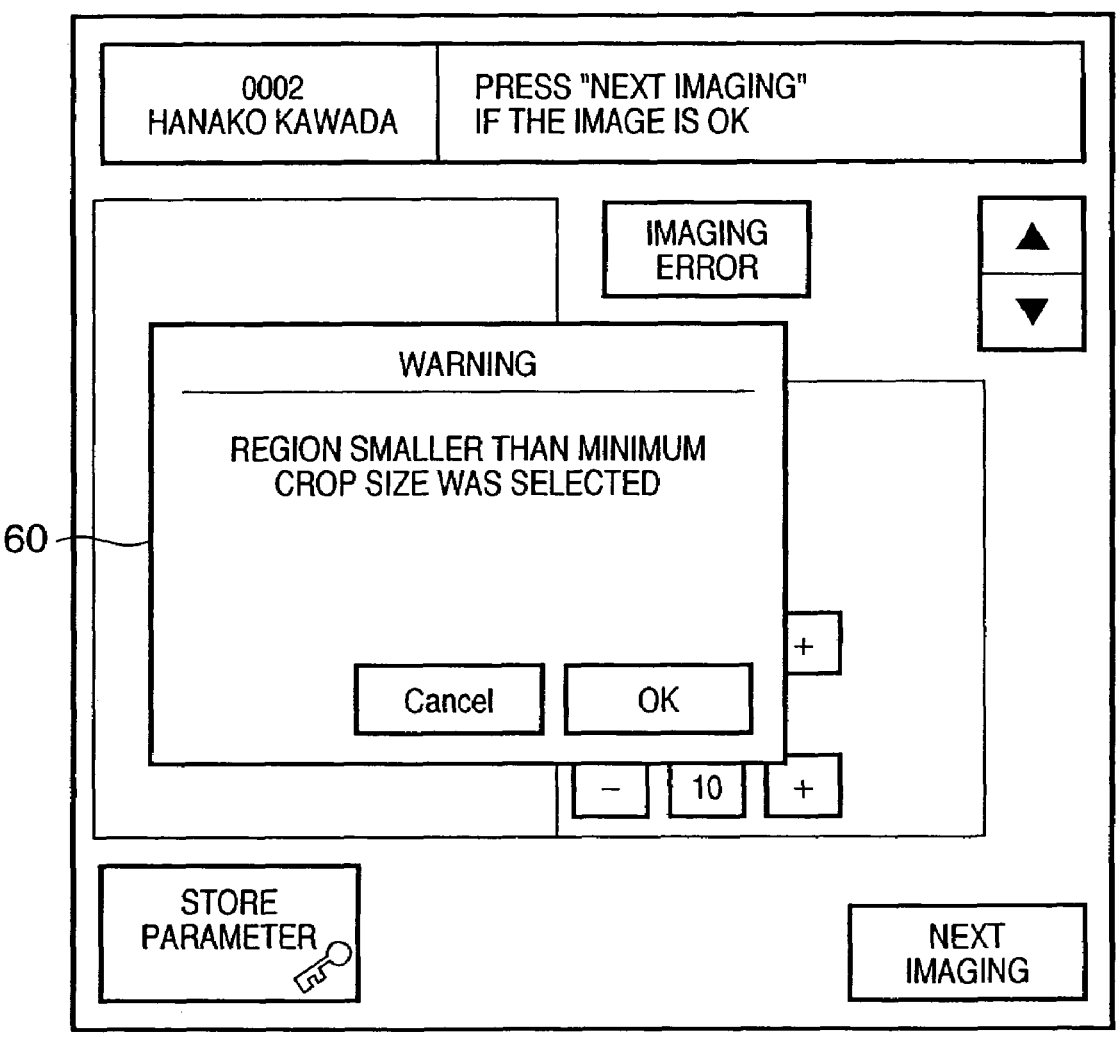
FIG. 6 is a view showing a display example of a warning generated after cropping.

If it is determined in step S110 that the extracted region is valid, the flow advances to step S115. If it is determined that the region is invalid, the flow advances to step S111 to execute notification processing (e.g., generating a warning accompanied by a warning window display 60 shown in FIG. 6 or a sound). After notification processing in step S111, the flow returns to step S108. If the operator gives an crop instruction again, the flow advances to step S109.

In determining in step S110 whether the extracted region is valid or invalid, at least one of the following processes (i) to (iii) is executed.

(i) It is checked whether the number of pixels in an image in an extracted region in the vertical or horizontal direction is smaller than a threshold set in advance for each portion to be imaged. If the number of pixels is smaller than the preset threshold, notification processing is executed in step S111. Obviously, such thresholds for the respective portions to be imaged may be stored in the DB so as to be read out on the basis of portion information.

(ii) It is checked whether the area of an image in an extracted region is smaller than a threshold set in advance for each portion to be imaged. If the above area is smaller than the preset threshold, notification processing is executed in step S111. Obviously, such thresholds for the respective portions to be imaged may be stored in the DB so as to be read out on the basis of portion information.

(iii) It is checked whether an extracted region has a parameter feature (e.g., "finger") attached to an image designated in advance for each portion to be imaged. If the region does not have such a feature, notification processing is executed in step S111. For example, this feature indicates the area of a subject region from which a direct exposed region is deleted, the shape of the contour of the subject region, the variance value of pixel values in the subject, or the like, and is set for each portion. Obviously, such parameter features for the respective portions to be imaged may be stored in the DB so as to be read out on the basis of portion information.

Note that in the processes (i) to (iii), in performing notification processing in step S111, the color of an extracted region in the image is changed to reliably notify that the region is not a valid region. More specifically, if it is determined in step S108 that the operator gives no crop instruction, the flow advances to step S115 to check whether or not imaging based on the examination order is complete. If all imaging operations are complete, the flow advances to step S116 to execute examination end processing and close the examination information. If it is determined in step S115 that imaging based on the examination order is not complete, the flow returns to step S101. The processing in step S101 and subsequent steps is repeated until all the imaging operations are complete.

With the above steps, control is made to check whether an extracted region of an image obtained by imaging is valid and to avoid a failure by notifying the operator of the corresponding information.

Second Embodiment

According to the processing in the first embodiment, notification processing is performed in step S111 in FIG. 7. In contrast to this, the second embodiment will exemplify a case wherein an image region is displayed upon being expanded to a reduced region set in advance for each imaging method.

When an extracted region is to be evaluated in step S109, the minimum extracted region is set in advance to 1 cm for the imaging method "finger". As this value, the minimum image size of the data obtained by imaging the fingers of children is set. If the region designated by an operator is smaller than the set value, it is determined that the operator has made an operation error such as double-clicking, and the extracted region is displayed upon being expanded to the preset minimum region instead of notification (re-setting).

In addition, to show the user that the region has been automatically changed, the color of the selected/designated region displayed is changed from green to red. In this case, the selected frame is automatically expanded around the center of gravity of the region designated by the operator. In addition, the operator is notified of the crop error, and transmission of an invalid image is inhibited. Upon checking the evaluation result at the time of crop, the operator either designates a region again or starts the next imaging operation.

In addition, the above minimum extracted region can be set for each imaging method, and a valid region is set for each imaging portion.

In each embodiment described above, the control program stored in the hard disk is transferred to the RAM to be executed by the CPU. However, the present invention is not limited to this. The present invention may be implemented by using an arbitrary storage medium. In addition, the present invention may be implemented by a circuit which performs the same operation as that described above.

The present invention can be applied to a system constituted by a plurality of devices, or to an apparatus comprising a single device. Obviously, the object of the present invention is realized even by supplying a recording medium which records software program codes for realizing the functions of the above-described embodiments to a system or apparatus, and causing the computer (or a CPU) of the system or apparatus to read out and execute the program codes recorded on the recording medium. In this case, the program codes read out from the recording medium realize the functions of the above-described embodiments by themselves, and the recording medium which records the program codes constitutes the present invention.

As a recording medium for supplying the program codes, a hard disk, optical disk, magnetooptical disk, CD-ROM, CD-R, magnetic tape, nonvolatile memory card, ROM, or the like can be used. Obviously, the functions of the above-described embodiments are realized not only when the readout program codes are executed by the computer but also when the OS running on the computer performs part or all of actual processing on the basis of the instructions of the program codes.

In addition, the functions of the above-described embodiments are also realized when the program codes read out from the storage medium are written in the memory of a function expansion board inserted into the computer or a function expansion unit connected to the computer, and the CPU of the function expansion board or function expansion unit performs part or all of actual processing on the basis of the instructions of the program codes.

Note that the present invention can also be applied to a case wherein the software program codes for implementing the functions of the above-described embodiments are recorded on a storage medium, and the program codes are distributed from the storage medium to each person who requests them through a communication line such as the Internet.

The present invention is not limited to the above embodiments and various changes and modifications can be made within the spirit and scope of the present invention. Therefore, to apprise the public of the scope of the present invention, the following claims are made.

What is claimed is:

1. An imaging apparatus in an image processing apparatus which has a function of determining whether a designated radiation field region is correct, comprising:
    designation means for designating a radiation field region from an image obtained by imaging on the basis of user instruction;
    determination means for determining that the designated region is invalid when the designated region does not have a characteristic feature of the radiation field region attached to a pre-designated image;
    notification means for notifying a determination result obtained by said determination means; and
    setting means for resetting the designated region to a preset region size when said determination means determines that the designated region is invalid,
    wherein the preset region size is determined on the basis of an imaging portion of the image obtained by imaging.

2. The apparatus according to claim 1, wherein said determination means determines whether the number of pixels in the image region designated by said designation means in a vertical direction or a horizontal direction is smaller than a threshold set in advance for each portion to be imaged, and if the number of pixels is smaller than the preset threshold, said notification means performs notification.

3. The apparatus according to claim 1, wherein said determination means determines whether an area of the image region designated by said designation means is smaller than a preset threshold, and if the area is smaller than the preset threshold, said notification means performs notification.

4. The apparatus according to claim 1, wherein said notification means changes a color of the image region designated by said designation means to notify that the region is not a valid region.

5. A computer-readable storage medium storing thereon a computer-executable program for causing a computer to control an imaging apparatus as defined in claim 1.

6. An imaging method comprising:
    the followings steps executed by a computer as an image processing apparatus which has a function of determining whether a designated radiation field region is correct,
    a designation step of designating a predetermined image region from an image obtained by imaging on the basis of user instruction;
    a determination step of determining that the designated region is invalid when the designated region does not have a characteristic feature of the radiation field region attached to a pre-designated image;
    a notification step of notifying a determination result obtained in the determination step; and
    a setting step of resetting the designated region to a preset region size when the designated region is determined to be invalid in said determination step,
    wherein the preset region size is determined on the basis of an imaging portion of the image obtained by imaging.

7. The method according to claim 6, wherein in the determination step, it is determined whether the number of pixels in the image region designated in the designation step in a vertical direction or a horizontal direction is smaller than a threshold set in advance for each portion to be imaged, and in the notification step, if the number of pixels is smaller than the preset threshold, notification is performed.

8. The method according to claim 6, wherein in the determination step, it is determined whether an area of the image region designated by the designation step is smaller than a preset threshold, and in the notification step, if the area is smaller than the preset threshold, notification is performed.

9. The method according to claim 6, wherein in the notification step, a color of the image region designated in the designation step is changed to notify that the region is not a valid region.

10. A computer-readable storage medium storing thereon a computer-executable program for causing a computer to execute an imaging method as defined in claim 6.

* * * * *